United States Patent
Bramanti

(10) Patent No.: US 9,983,169 B2
(45) Date of Patent: May 29, 2018

(54) INTEGRATED MICROFLUIDIC CIRCUIT WITH ELECTROWETTING-BASED OPERATION AND CORRESPONDING MICROFLUIDIC SYSTEM

(71) Applicant: STMICROELECTRONICS S.R.L., Agrate Brianza (IT)

(72) Inventor: Alessandro Paolo Bramanti, Maglie (IT)

(73) Assignee: STMICROELECTRONICS S.R.L., Agrate Brianza (IT)

( * ) Notice: Subject to any disclaimer, the term of this patent is extended or adjusted under 35 U.S.C. 154(b) by 205 days.

(21) Appl. No.: 14/489,310

(22) Filed: Sep. 17, 2014

(65) Prior Publication Data
US 2015/0075988 A1   Mar. 19, 2015

(30) Foreign Application Priority Data

Sep. 17, 2013  (IT) .............................. TO2013A0757

(51) Int. Cl.
*G01N 27/447* (2006.01)
*B81B 1/00* (2006.01)
(Continued)

(52) U.S. Cl.
CPC .... *G01N 27/44791* (2013.01); *B01L 3/50273* (2013.01); *B81B 1/00* (2013.01);
(Continued)

(58) Field of Classification Search
CPC ..... B01L 2300/0816; B01L 2400/0427; B01L 3/50273; B81B 1/00; G01N 27/44791; G01N 27/453
See application file for complete search history.

(56) References Cited

U.S. PATENT DOCUMENTS

| | | | |
|---|---|---|---|
| 2008/0169195 A1* | 7/2008 | Jones ................ | B01L 3/0268 204/547 |
| 2010/0096266 A1* | 4/2010 | Kim .................. | B01F 13/0071 204/451 |

(Continued)

FOREIGN PATENT DOCUMENTS

| | | |
|---|---|---|
| DE | 10 2008 019 585 A1 | 11/2009 |
| WO | 2009/052354 A2 | 4/2009 |

OTHER PUBLICATIONS

Duke University, Duke Microfluidics Lab, "Publications," retrieved from URL=http://microfluidics.ee.duke.edu/publications.html on Dec. 17, 2014, 9 pages.

(Continued)

*Primary Examiner* — Louis J Rufo
(74) *Attorney, Agent, or Firm* — Seed Intellectual Property Law Group LLP

(57) ABSTRACT

An integrated fluidic circuit has a supporting surface that carries a first fluid to be moved at a first functional region; a dielectric structure, defining the supporting surface; and an electrode structure, coupled to the dielectric structure for generating an electric field at the first functional region, such as to modify electrowetting properties of the interface between the first fluid and the supporting surface. The dielectric structure has a first spatially variable dielectric profile at the first functional region, thus determining a corresponding spatially variable profile of the electric field, and, consequently, of the electrowetting properties of the interface between the first fluid and the supporting surface. The integrated fluidic circuit may achieve mixing between the first fluid and a second fluid.

20 Claims, 14 Drawing Sheets

(51) Int. Cl.
*G01N 27/453* (2006.01)
*B01L 3/00* (2006.01)

(52) U.S. Cl.
CPC .... *G01N 27/453* (2013.01); *B01L 2300/0816* (2013.01); *B01L 2400/0427* (2013.01)

(56) References Cited

U.S. PATENT DOCUMENTS

| | | | |
|---|---|---|---|
| 2010/0236927 A1* | 9/2010 | Pope | B01L 3/502792 204/450 |
| 2011/0147216 A1* | 6/2011 | Fan | B01J 13/04 204/451 |
| 2014/0145751 A1 | 5/2014 | Bramanti | |

OTHER PUBLICATIONS

Cannara et al., "Thermo-mechanical probe storage at Mbps single-probe data rates and Tbit in $^{-2}$ densities," *Nanotechnology 19*:395305, 2008, 6 pages.

Fan et al., "Low-Temperature-Deposited $SiO_2$ Gate Insulator with Hydrophobic Methyl Groups for Bottom-Contact Organic Thin0Film Transistors," *IEEE Electron Device Letters 31*(12):1485-1487, Dec. 2010.

Hanisch et al., "All-sputtered contacts for organic solar cells," *This Solid Films 516*:7241-7244, 2008.

Lee et al., "Microbioreactor arrays with integrated mixers and fluid injectors for high-throughput experimentation with pH and dissolved oxygen control," *Lab Chip 6*:1229-1235, 2006.

Lin et al., "Leakage current and breakdown electric-field studies on ultrathin atomic-layer-deposited $Al_2O_3$ on GaAs," *Applied Physics Letters 87*:182904, 2005, 3 pages.

Lu et al., "High-k Polymer Nanocomposites as Gate Dielectrics for Organic Electronics Applications," 2007 Electronic Components and Technology Conference, pp. 453-457, 2007.

Renaudot et al., "Performances of High-K Dielectric Materials ($Al_2O_3$, $HfO_2$, $ZrO_2$) for Liquid Dielectrophoresis (LDEP) Microfluidic Devices," 16$^{th}$ International Conference on Miniaturized Systems for Chemistry and Life Sciences, Oct. 28-Nov. 1, 2012, Okinawa, Japan, pp. 905-907.

* cited by examiner

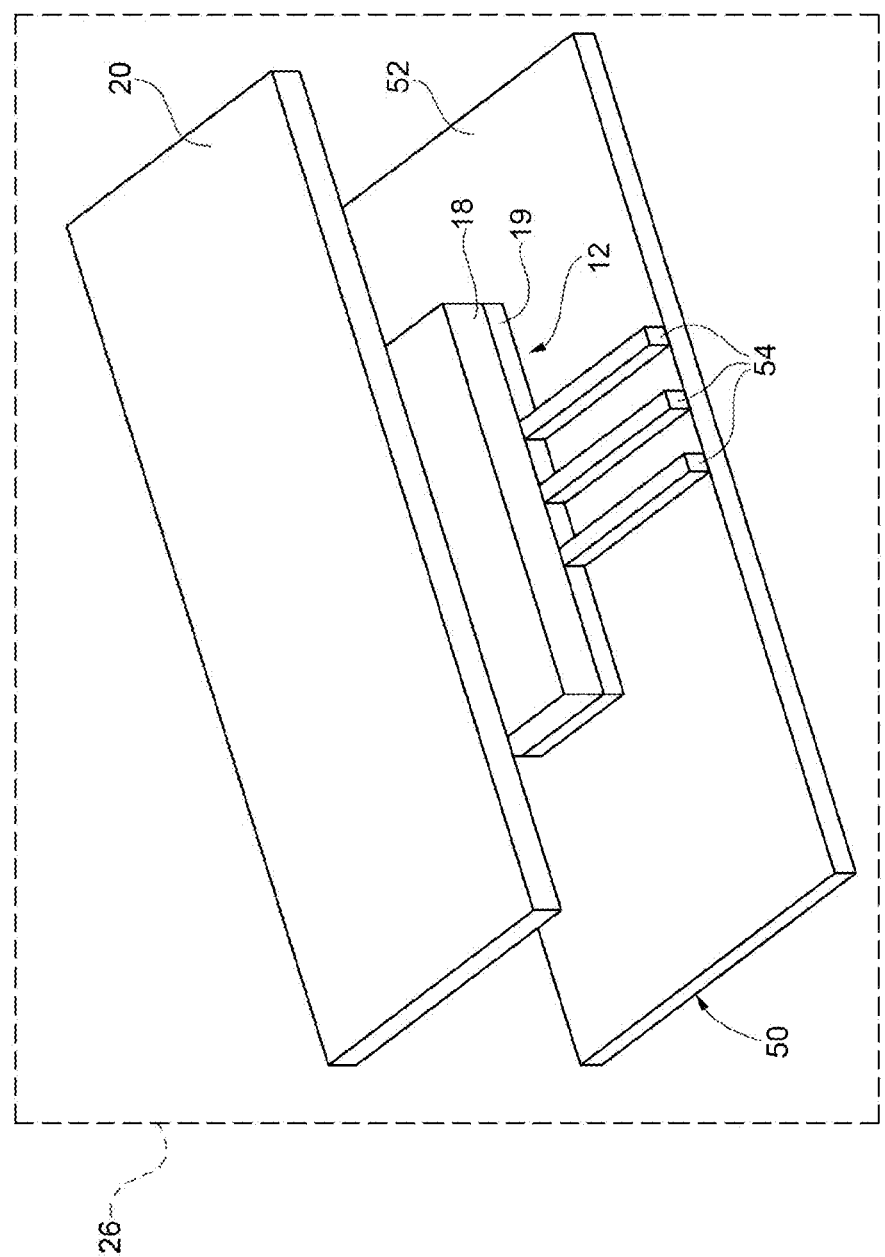

INTEGRATED MICROFLUIDIC CIRCUIT WITH ELECTROWETTING-BASED OPERATION AND CORRESPONDING MICROFLUIDIC SYSTEM

BACKGROUND

Technical Field

The present disclosure relates to an integrated microfluidic circuit with electrowetting-based operation and a corresponding microfluidic system.

Description of the Related Art

Known is the increasing use of integrated microfluidic circuits, for example manufactured with semiconductor materials and using MEMS (MicroElectroMechanical Systems) techniques, to obtain so-called "labs-on-chip".

Lab-on-chip microfluidic analysis devices are used for carrying out chemical reactions on extremely small amounts of substances, for example, but not only, in the medical field, and in the field of diagnostics and follow-up.

Some advantages of the above devices consist in the considerable reduction of size and costs as compared to traditional solutions for laboratory analysis, in the speed of response, and in the reduction of the amount of specimens that are to be analyzed.

Integrated microfluidic circuits used in lab-on-chip devices include, for example, transport circuits, controlled-flow circuits, confinement circuits, circuits for mixing fluids, or, in general, circuits for actuation of one or more fluids.

It is also known that one of the major difficulties in manufacturing integrated microfluidic circuits lies in the integration of suitable actuators for movement of the fluids, such as valves, pumps, or actuation devices in general.

For the above purpose, some known solutions envisage the use of micromechanical actuators, i.e., ones based on mechanical deformations and movements on a micrometric or submicrometric scale. These solutions are not, however, altogether satisfactory, in particular as regards the complexity of implementation and the difficulties in the reduction of costs and size.

In order to overcome the above problems, other solutions that have been proposed envisage exploiting the so-called "electrowetting" phenomenon, i.e., the property of an electric field to modify the surface tension of a liquid, by introducing a term of electrostatic energy in the energy balance of the system constituted by the liquid and the surface of solid material with which the liquid is in contact.

In greater detail, and with reference to FIG. 1a, in the absence of an electric field, the contact surface between a supporting material, designated by 2, and a given amount of liquid 3, is hydrophobic. In other words, the contact angle θ between the liquid and the surface is greater than 90°.

Upon application of an electric field E (FIG. 1b), achieving a better condition in terms of energy balance entails a reduction of the value of the contact angle θ. In the case where the angle of contact θ is less than 90°, the contact surface 2 becomes hydrophilic, bringing about a "flattening" of the amount of liquid 3 on the contact surface 2, which is all the more marked the lower the value of contact angle θ.

Integrated microfluidic circuits based on the phenomenon described above in general envisage the use of a set of adjacent electrodes, which can be controlled individually from the electrical standpoint.

The electrodes define, on the surface of a supporting substrate to which they are coupled, fluidic paths, along which drops (or "packets") of fluid are conveyed by selective turning-on or turning-off of adjacent electrodes. In fact, the local generation of electric fields by turning on the electrodes enables activation or deactivation of the electrowetting characteristics of the portions of substrate located at the same electrodes, which are each time rendered hydrophobic or hydrophilic, thus attracting or repelling the drops or packets of fluid.

Solutions for fluidic transport of the above sort are frequently defined as solutions of "digital microfluidics", given the on/off characteristic of the achieved transport mode.

A detailed description of these solutions may be found, for example, at: http://microfluidics.ee.duke.edu, by Duke University, Durham, N.C.

Also these solutions are not, however, free from defects and problems.

In particular, the resolution (in terms of the minimum amount of fluid that can be moved) of a microfluidic circuit obtained in this way is dictated by the minimum size of the electrodes, which represent in general the "pixel" or elementary unit of movement of the fluid, thus determining the amount of the fluid and the spatial resolution of the circuit.

Moreover, each electrode is connected to an electrical supply source by means of an appropriate electrical connection element. This entails a considerable complexity of the resulting electrical connections, an increase in the occupation of area, the presence of geometrical constraints, and possibly an additional metal layer.

Consequently, it is difficult to provide complex designs for the microfluidic circuits (for example, for the preparation of specimens for being analyzed on chips having small dimensions), and in any case these circuits have a high occupation of area.

In addition, if a mixer for fluids is made with the solution described, the composition of the mixed fluid is a function of the ratio of a certain integer number m of drops (or packets) of a first fluid, and of a respective integer number n of drops (or packets) of a second fluid.

In particular, the minimum amount of fluid that can be mixed with a mixing ratio m:n is (m+n)·d, where d is the volume of an individual drop (or packet) of fluid, which is a function, as previously highlighted, of the characteristics of the electrodes.

Consequently, mixing of the fluids can be carried out only in a discrete way, which is not finely tunable, as a function of the volume d of the individual packet of fluid that can be moved.

Recent studies seem also to indicate that the same volume of fluid that can be transported by each pixel or elementary electrode unit is not always repeatable, precise, and constant over time, with consequent possible imprecision in the movement and management of the fluids.

BRIEF SUMMARY

One embodiment of the present disclosure is directed to an integrated fluidic circuit that includes a dielectric structure having a supporting surface of an electrowettable material on a first side of the dielectric structure, a first electrode structure separated from the dielectric structure by a gap, and a second electrode structure on a second side of the dielectric structure, the supporting surface being between the first and second electrode structures, the second electrode structure configured to be coupled to the first electrode structure to generate an electric field at a first functional region to modify electrowetting properties of a first fluid between the first electrode structure and the supporting surface, the dielectric structure having a varying thickness between the second electrode and the supporting surface in the first functional region, the varying thickness being configured to affect the electric field between the first and second electrode structures.

BRIEF DESCRIPTION OF THE SEVERAL VIEWS OF THE DRAWINGS

For a better understanding of the present invention, preferred embodiments thereof are now described, purely by way of non-limiting example and with reference to the attached drawings, wherein:

FIG. 20 is a schematic perspective view of a microfluidic device according to a further aspect of the invention.

DETAILED DESCRIPTION

Figure 1A:
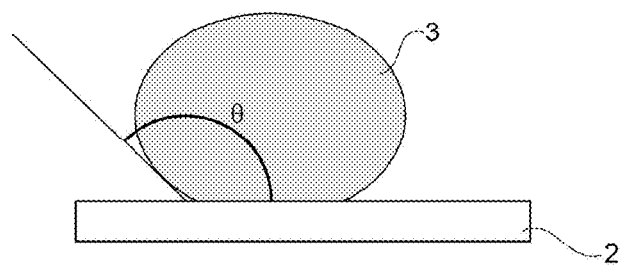
FIGS. 1a and 1b show schematic representations of an amount of fluid on a supporting surface, highlighting the electrowetting phenomenon.
Figure 1B:
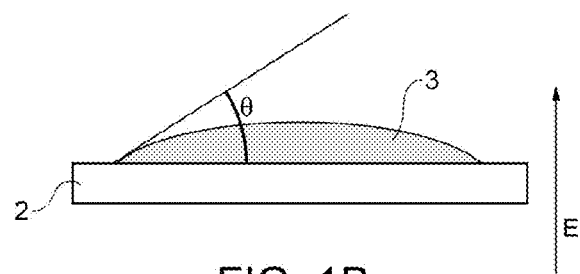
Figure 2:
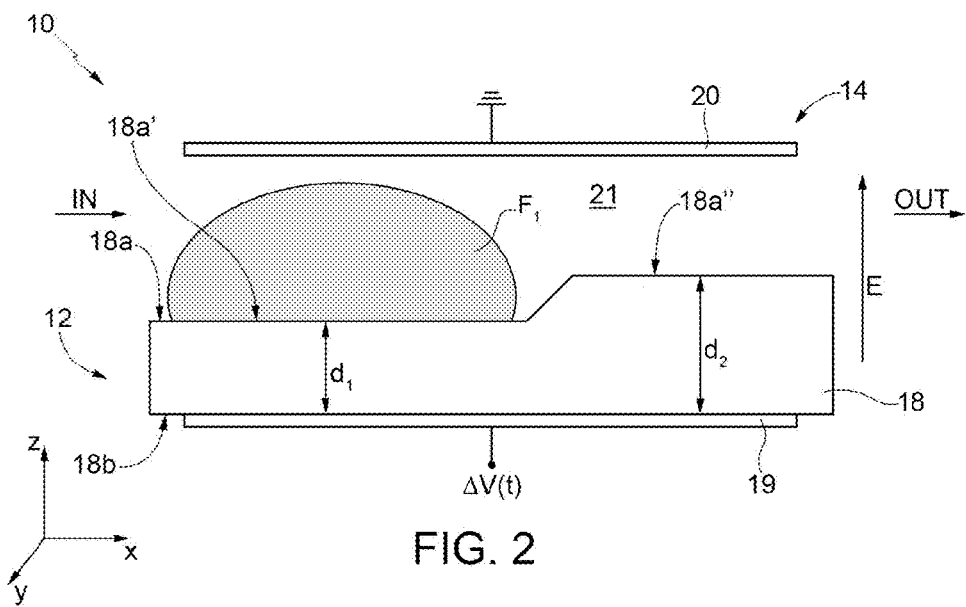
FIG. 2 is a cross section of a microfluidic circuit according to one embodiment of the invention.

With reference to FIG. 2, a first embodiment of a microfluidic circuit is now described, designated as a whole by 10, obtained in an integrated manner with the techniques proper to the semiconductor industry.

The microfluidic circuit 10 has an inlet IN, at which it receives a first amount (for example, a drop or packet) of a fluid $F_1$ to be moved, and an outlet OUT, at which it supplies selectively and in a controlled way a second desired amount of the same fluid $F_1$.

In detail, the microfluidic circuit 10 comprises a dielectric structure 12, and an electrode structure 14, coupled to the dielectric structure 12 so as to generate, at the same dielectric structure 12, a desired electric field E.

The dielectric structure 12 comprises, in the embodiment illustrated in FIG. 2, a single dielectric layer 18, made, for example, of PTFE (Teflon), hydrophobic $SiO_2$, $Al_2O_3$ (ALD—Atomic Layer Deposited aluminum oxide), or Parylene; the dielectric layer 18 has electrowetting properties.

In particular, the dielectric layer 18 has a spatially variable conformation, at a first surface thereof, in the example a top surface 18a, opposite (along a vertical axis z) to a bottom surface 18b, set in contact with the electrode structure 14. In use, the fluid $F_1$ is placed on the top surface 18a of the dielectric layer 18.

The dielectric structure 12 hence has a dielectric profile (or gradient) that is spatially variable at a functional, or actuation, region of the top surface 18a of the dielectric layer 18, i.e., a region where a movement of the fluid $F_1$ is to be generated. In general, the dielectric profile is variable along the direction where the movement of the fluid $F_1$ is to be generated.

In particular, the top surface 18a is constituted by a first portion 18a' and a second portion 18a" that are substantially planar (in a horizontal plane xy, orthogonal to the vertical axis z and defined by horizontal axes x and y), joined by an inclined portion, set at a certain desired angle with respect to the horizontal plane xy and to the vertical axis z.

The dielectric layer 18 thus has a first thickness $d_1$ at the first portion 18a' of the top surface 18a, and a second thickness $d_2$, greater than the first thickness $d_1$, at the second portion 18a".

The electrode structure 14 comprises: a first control electrode 19, which is substantially planar (in the horizontal plane xy), set in contact with the bottom surface 18b of the dielectric layer 18; and a reference electrode (or counter-electrode) 20, which is also substantially planar (in the horizontal plane xy), set at a distance from the top surface 18a of the dielectric layer 18, defining a gap 21, including, for example, air, within which the fluid $F_1$ is located and moves during operation.

In the microfluidic circuit 10, the electric field E is thus temporally and spatially variable.

In particular, the variability in time is given by the corresponding variability of a potential difference $\Delta V(t)$ applied to the electrode structure 14 (by means of a suitable signal generator, not illustrated), between the first control electrode 19 and the reference electrode 20 (which, for example, is connected to a reference potential, such as the electrical ground of the circuit).

The variability in space is, instead, defined by the spatially variable conformation of the dielectric structure 12, which defines, in the embodiment illustrated in FIG. 2, a dielectric profile, or gradient, along the horizontal axis x.

The electrowetting characteristics of the top surface 18a of the dielectric layer 18 are, accordingly, variable both in time and in space.

Advantageously, the aforesaid electrowetting is hence tunable in a fine and precise manner, thanks to the possibility of suitably modulating the applied potential difference $\Delta V(t)$, based on the conformation of the dielectric structure 12.

In greater detail, in the embodiment illustrated in FIG. 2, the conformation of the dielectric structure 12 basically defines two capacitors with plane and parallel faces (defined respectively at the first portion 18a' and the second portion 18a" of the top surface 18a of the dielectric layer 18). Moreover, also to the inclined portion of the top surface 18a, a lumped-element model can be applied, approximating the effect of the dielectric as a locally variable planar capacitance.

Using Young's equation, upon application of the potential difference $\Delta V(t)$, it may be shown that the contact angle $\theta$ (which defines the electrowetting characteristics) varies according to the following expression:

$$\theta(x,t) = \arccos\left(\cos\theta_0 + \frac{\varepsilon_0 \varepsilon_{r1} d(x)}{2\gamma_{LV}} E^2(x,t)\right)$$

where $\theta_0$ is the initial angle of contact (for example, in the case where the fluid is deionized water and the dielectric is $Al_2O_3$, $\theta_0$ is 90°); $\varepsilon_{r1}$ is the relative permittivity of the dielectric layer 18; $\gamma_{LV}$ is the liquid-vapor tension of the fluid $F_1$, equal for example to 0.072 $Jm^{-2}$ in the case of water; $d(x)$ is the thickness of the dielectric layer 18, variable according to the position along the horizontal axis x; and $E(x,t)$ is the electric field that acts on the dielectric layer 18 and that is felt by the fluid $F_1$, which also depends on the position along the horizontal axis x and moreover on time, by virtue of the dependence upon the potential difference $\Delta V(t)$, approximately according to the expression $E(x,t)=\Delta V(t)/d(x)$, and the value of which can be obtained point by point by numeric simulation, for example employing a finite-element model (FEM).

It is known that electrowettable materials generally have a limit value of the contact angle (referred to as "saturation angle") between 30° and 80°, which the above equation does not take into account. For the following considerations, the saturation angle will be ignored or, equivalently, it will be assumed that the electric field E is not such as to saturate the wettability and consequently such as to remain within the range of validity of the equation. This assumption simplifies the interpretation of the results and is independent of any particular hypotheses regarding the material, without in any case vitiating the conclusions that can be derived from the results.

Figure 3A:
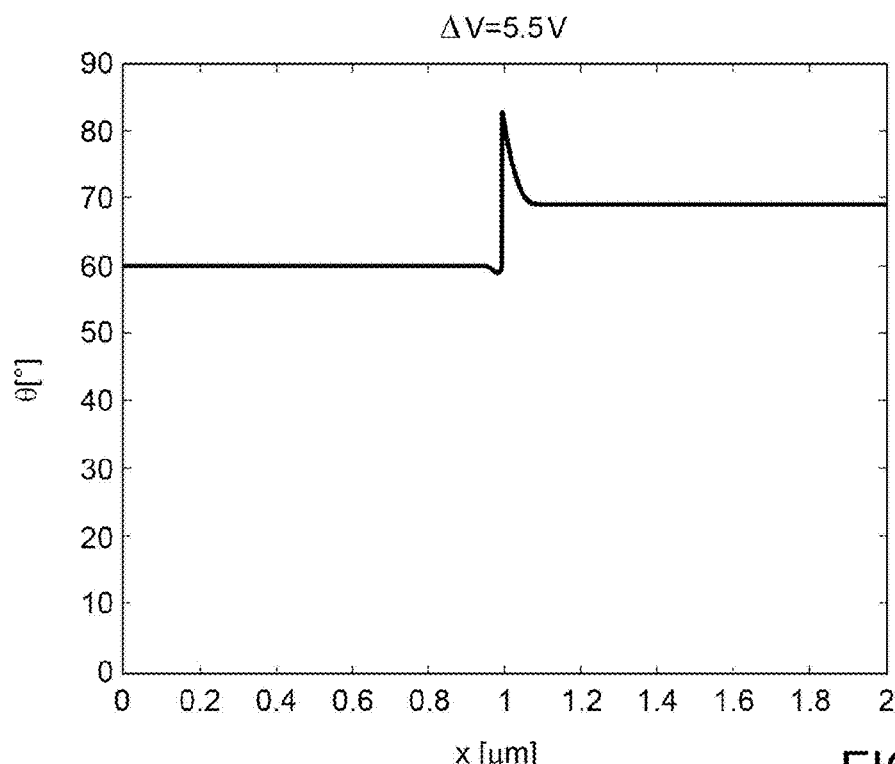
FIGS. 3a, 3b, and 4 show plots of quantities related to the microfluidic circuit of FIG. 2.
Figure 3B:
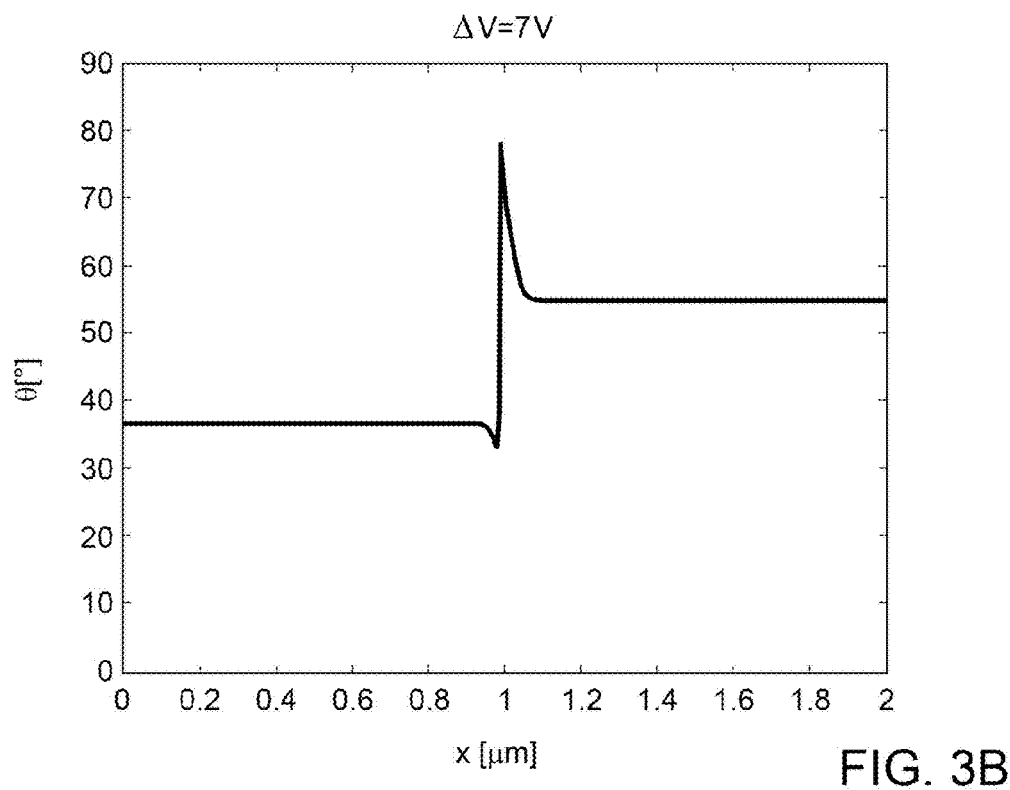

FIGS. 3a and 3b show the plots of the contact angle $\theta$ as the position along the horizontal axis x varies (0 indicating the position of the inlet IN) in the presence of a potential difference $\Delta V$ of 5.5 V and, respectively, 7 V.

The contact angle $\theta$ is in all cases smaller at the first portion 18a' of the top surface 18a of the dielectric layer 18 as compared to the second portion 18a"; however, as the value of the potential difference $\Delta V$ increases, the contact angle $\theta$ decreases considerably (in particular, in the example, it becomes less than 60°) at both of the portions 18a', 18a", which hence both become wettable.

In a model that were to take into account the saturation angle of the material, it would be possible to determine a value of electric field E such as to bring the wettability to saturation in both of the portions, i.e., such as to render them both as wettable as possible.

Figure 4:
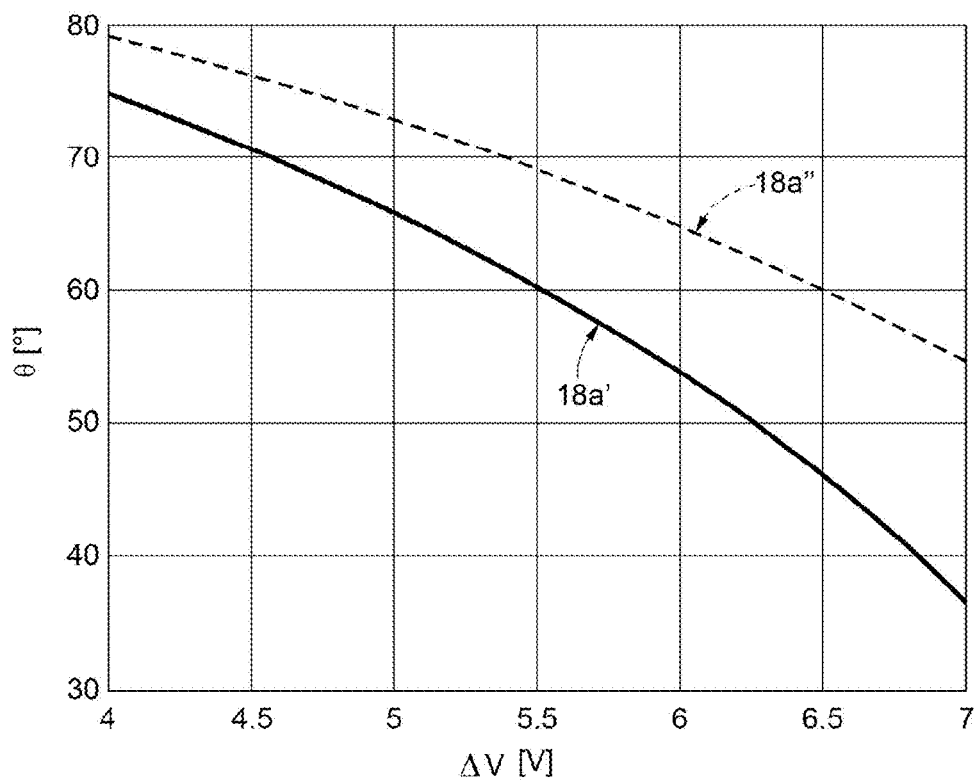

FIG. 4 shows the plot of the contact angle $\theta$ at the first portion 18a' and at the second portion 18a", respectively, of the top surface 18a of the dielectric layer 18, as the value of the potential difference $\Delta V$ varies.

It is thus evident that the wettability of the surface of the dielectric layer 18 may be controlled precisely as a function of the value of the potential difference $\Delta V(t)$ applied to the electrode structure 14, and moreover of the spatial conformation of the dielectric layer 18.

In particular, the spatial evolution of the value of wettability corresponds to the spatial conformation of the dielectric structure 12, which hence defines the region of transport for the fluid $F_1$ on the top surface 18a of the dielectric layer 18 (in other words, defining a sort of "confinement" or channel region in which the fluid $F_1$ can be moved with desired characteristics). It is emphasized that this confinement is to be understood not in the physical sense, but in the energy sense, in so far as it originates from the spatial variability of the value of the electric field E and from the spatial selectivity of the resulting electrowetting properties.

The microfluidic circuit 10 may, for example, be used to obtain transport of a desired amount of fluid along the horizontal axis x.

Figure 5:
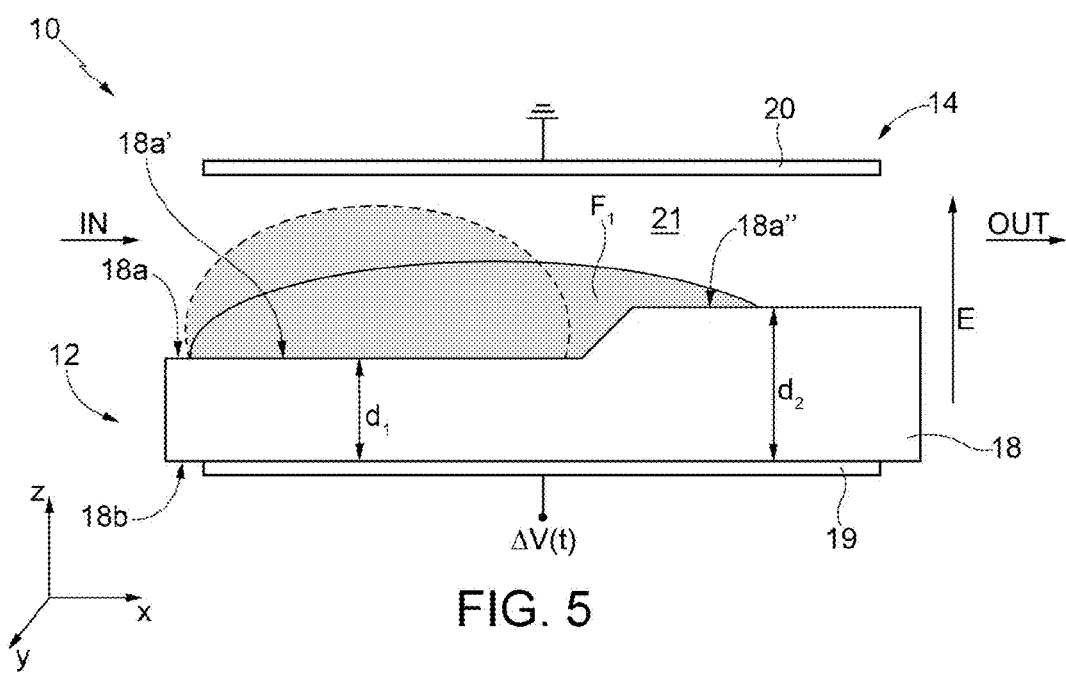
FIG. 5 is a cross section of the microfluidic circuit of FIG. 2, in a different operating condition.

Represented in FIG. 5 with a dashed line is a first operating condition in which a drop (or packet) of fluid $F_1$ is at the first portion 18a' of the top surface 18a of the dielectric layer 18, in the presence of a first value $\Delta V_1$ of the potential difference $\Delta V(t)$.

Represented, instead, with a solid line is a second operating condition (subsequent to the first), where the potential difference $\Delta V(t)$ has been incremented to a second value $\Delta V_2$, greater than the first value $\Delta V_1$. As a result of the smaller value assumed by the contact angle $\theta$, the top surface 18a of the dielectric layer 18 becomes more wettable, and the drop of fluid $F_1$ expands, i.e., widens, on the surface, also in the second portion 18a" of the top surface 18a (passing beyond the inclined portion).

Figure 6A:
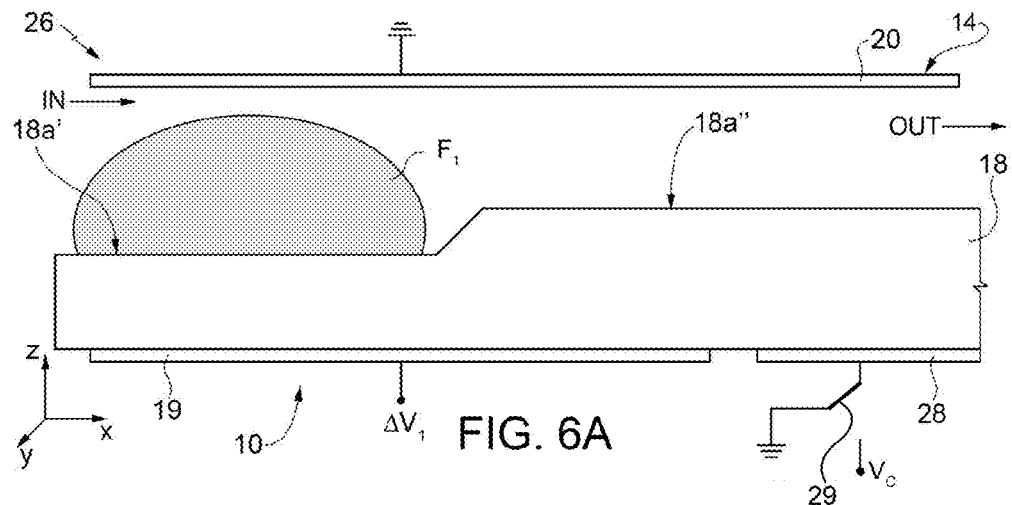
FIGS. 6a-6c show sections, corresponding to different operating conditions, of an embodiment of a microfluidic device.

FIG. 6a shows, in a first operating condition, a microfluidic device 26, which includes the microfluidic circuit 10, to provide a finely tunable flow valve.

The microfluidic device 26 further comprises a second control electrode 28, set in contact with the bottom surface 18b of the dielectric layer 18, alongside the first control electrode 19 at a certain distance therefrom along the horizontal axis x. The second control electrode 28 is located at a prolongation of the second portion 18a" of the top surface 18a of the dielectric layer 18.

The second control electrode 28 is selectively set at a control voltage $V_c$ or at a reference voltage (ground), by opening/closing of a switch element 29. The second control electrode 28 forms, with the reference electrode 20, a capacitor with plane and parallel faces.

Figure 6B:
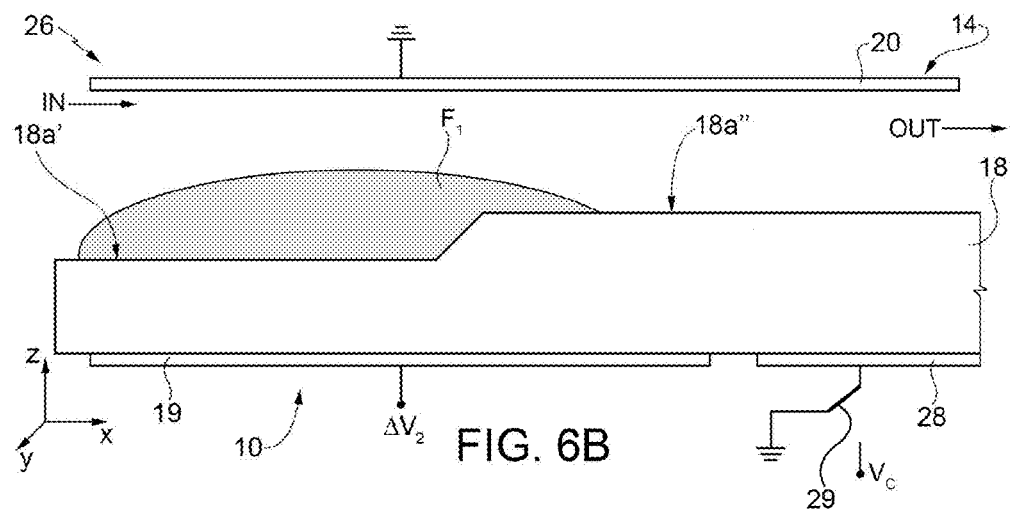

In use, the potential difference $\Delta V$, applied between the first control electrode 19 and the reference electrode 20, is progressively incremented from a value $\Delta V_1$ to a value $\Delta V_2$ for widening the drop of fluid $F_1$, as illustrated previously (thus reaching a second operating condition, shown in FIG. 6b).

Figure 6C:
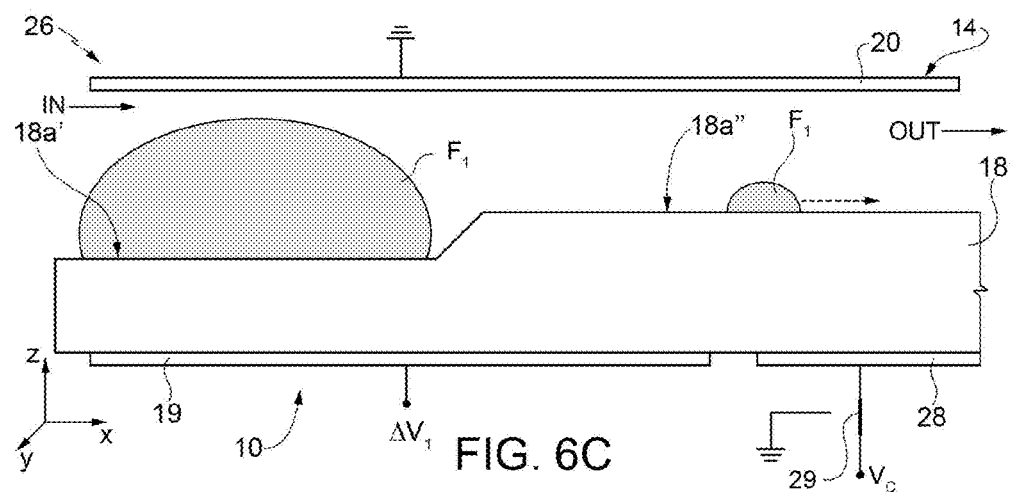

Then, the second control electrode 28 is set at the control voltage $V_c$, in such a way as to "attract" a part of the fluid $F_1$ at the prolongation of the second portion 18a" of the top surface 18a of the dielectric layer 18 (operating condition shown in FIG. 6c, where the potential difference $\Delta V$ is moreover brought to the value $\Delta V_1$ so that the remaining part of the fluid $F_1$ returns towards the first portion 18a' of the top surface 18a of the dielectric layer 18).

The microfluidic device 26 hence implements a valve, which enables selective passage of a controlled amount of fluid $F_1$ from the inlet IN to the outlet OUT; in particular, the value of the volume of fluid $F_1$ that traverses the valve following upon opening thereof is finely tunable as a function of the spatial conformation of the dielectric layer 18 and of the value of the potential difference ΔV(t) applied to the electrode structure 14 of the microfluidic circuit 10. When the value $\Delta V_2$ of the potential difference ΔV is incremented, the volume of fluid $F_1$ that traverses the valve is incremented accordingly.

Figure 7A:
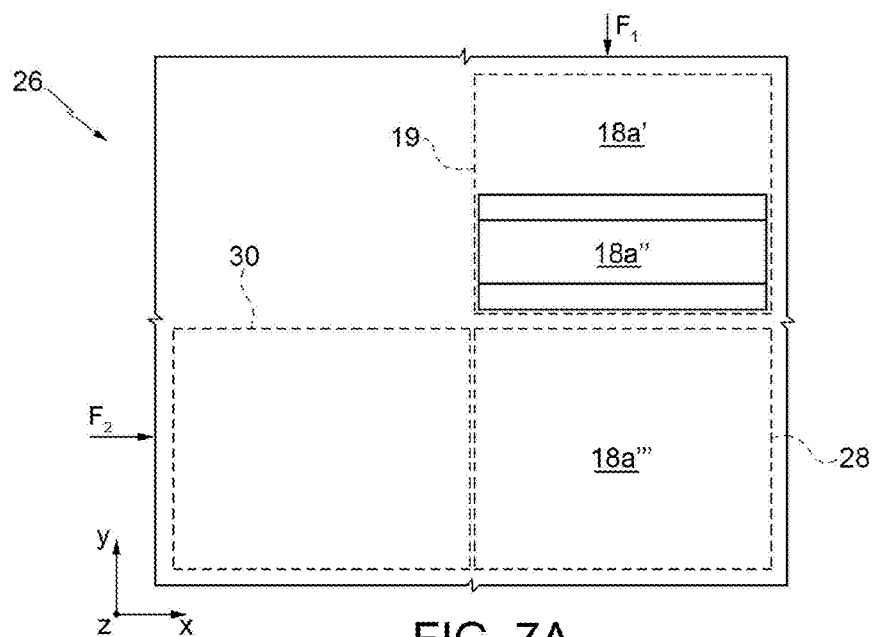
FIG. 7a is a schematic plan view of a further embodiment of a microfluidic device.
Figure 7B:
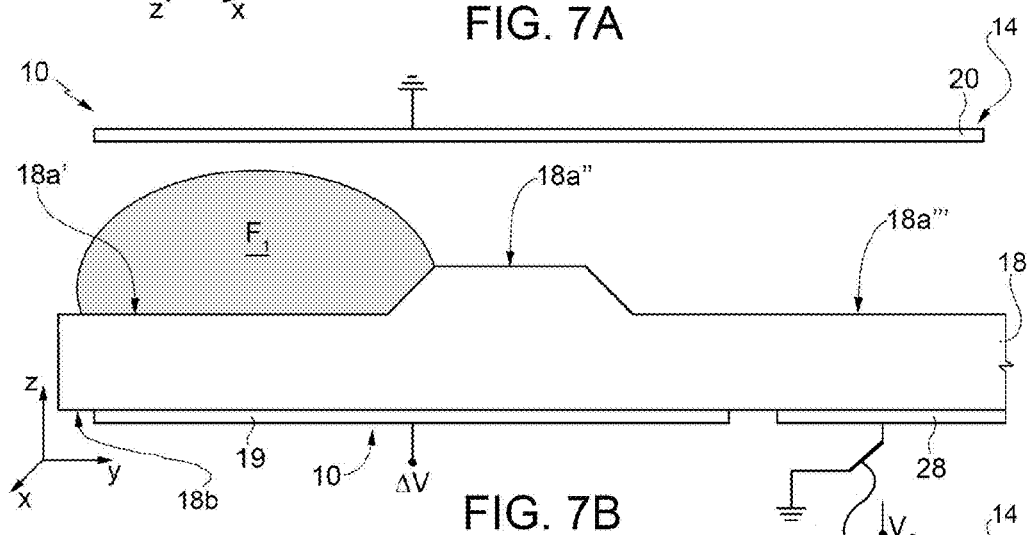
FIGS. 7b and 7c are sections of the device of FIG. 7a, taken respectively along the horizontal axis y and along the horizontal axis x.
Figure 7C:
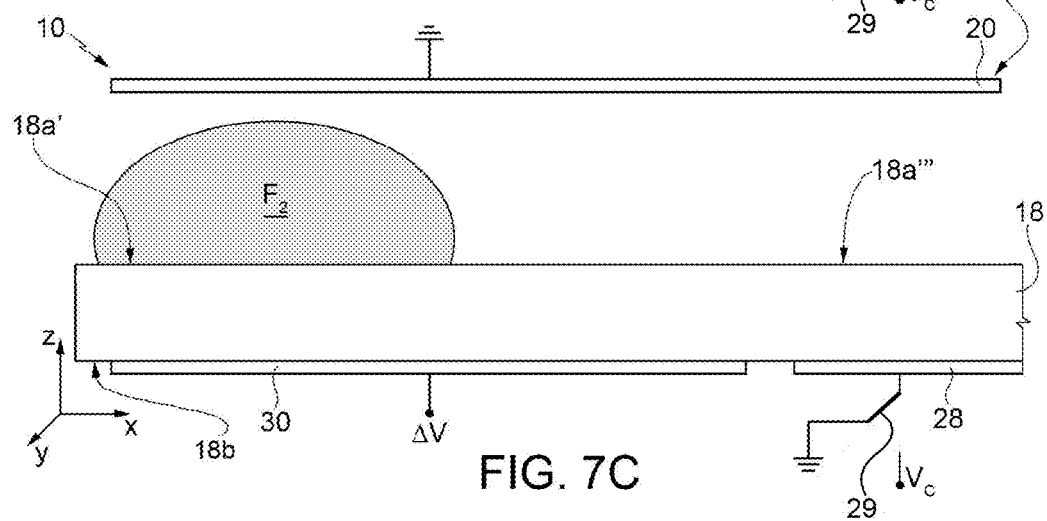

Represented schematically in FIGS. 7a, 7b, and 7c, respectively in a top plan view, in a first cross-sectional view taken along the horizontal axis y, and in a second cross-sectional view taken along the horizontal axis x, is a further embodiment of a microfluidic device, once again designated by 26, having in this case a mixer function.

The top surface 18a of the dielectric layer 18 has, in this case, in the cross section taken along the horizontal axis y, a third, substantially planar, portion 18a''' contiguous to the second portion 18a'' and having a thickness $d_1$ substantially equal to the thickness of the first portion 18a'.

Moreover, the microfluidic device 26 comprises a third control electrode 30, set in contact with the bottom surface 18b of the dielectric layer 18, alongside the second control electrode 28 along the horizontal axis x (as may be seen in the cross section taken along the horizontal axis x).

In use, the application of an appropriate potential difference ΔV to the first control electrode 19 enables a desired amount of a first fluid, designated once again by $F_1$, to overstep the energy "barrier" defined by the spatially variable value of the electric field E and to reach, upon application of a suitable voltage to the second control electrode 28, the area corresponding to the third portion 18a''' of the top surface 18a. It should hence be noted that in this way a first channel for transport of the first fluid $F_1$ is defined.

At the same time, or subsequently, application of an appropriate voltage to the third control electrode 30 enables a pre-set amount of a second fluid $F_2$ to reach the corresponding area of the top surface 18a of the dielectric layer 18, and then to reach the third portion 18a''' of the top surface 18a upon application of a suitable voltage to the second control electrode 28. It should hence be noted that a second channel for transport of the second fluid $F_2$ is thus defined, with different electrowetting properties of the dielectric layer 18 as compared to the first channel.

Mixing of an appropriate amount of the first fluid $F_1$ with the pre-set amount of the second fluid $F_2$ is consequently obtained, this mixing being controllable in an accurate way by a suitable conformation of the dielectric layer 18 and an appropriate choice of the values of voltage applied to the control electrodes.

It is evident that the potential difference ΔV(t) applied to the electrode structure 14 may have various waveforms, and the control may act on the amplitude, frequency, duty cycle, or different and further parameters of the waveforms.

Figure 8:
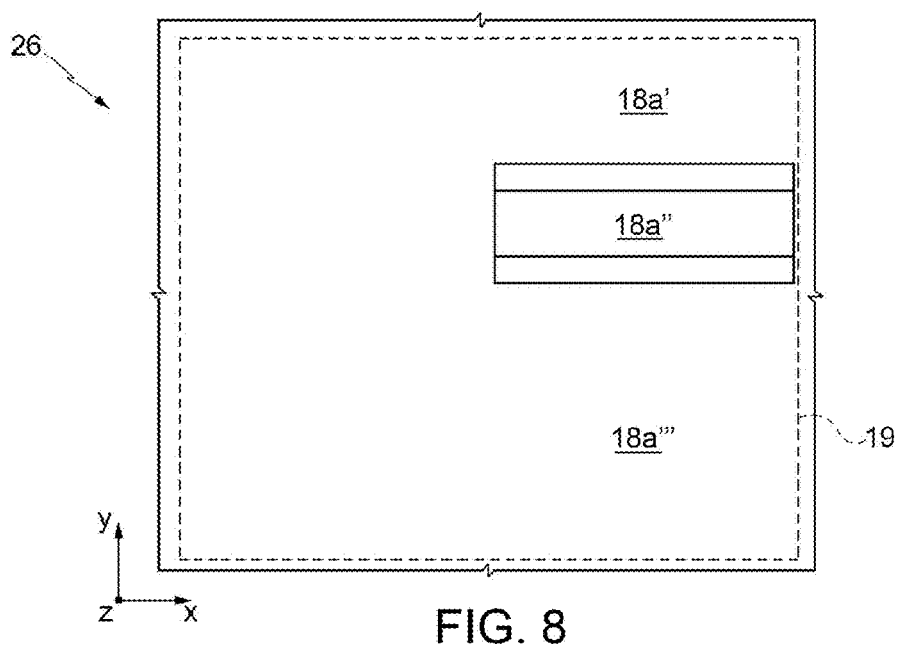
FIG. 8 is a schematic plan view of a further embodiment of a microfluidic device.

As illustrated in FIG. 8, another embodiment of the microfluidic device 26, having once again a mixing function, may envisage the use of a single control electrode, here designated by 19, which extends underneath the dielectric layer 18, at the first and second channels previously defined.

Figure 9A:
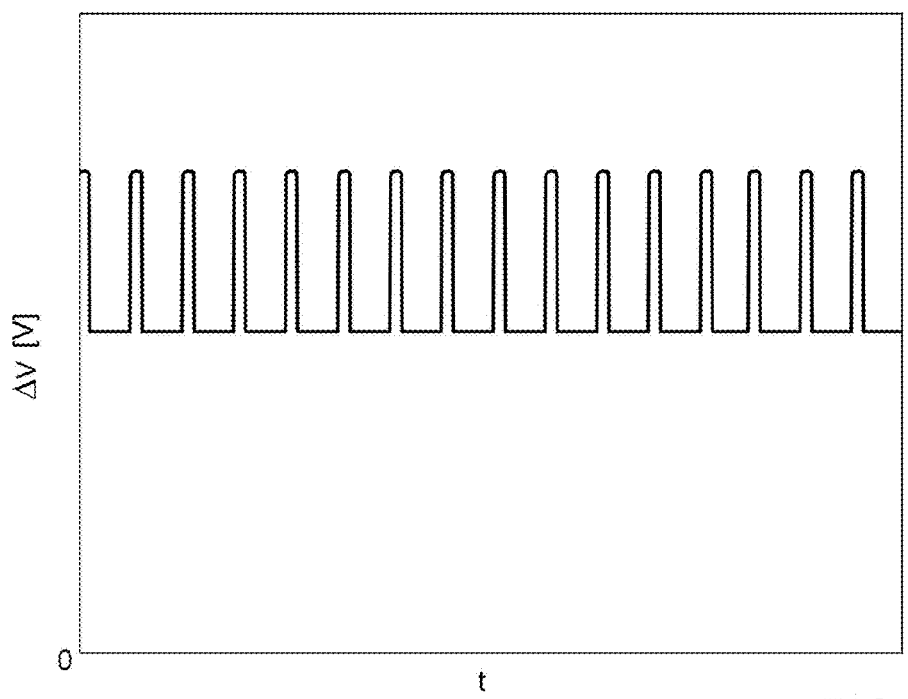
FIGS. 9a-9c show plots of quantities related to the microfluidic device of FIG. 8.
Figure 9B:
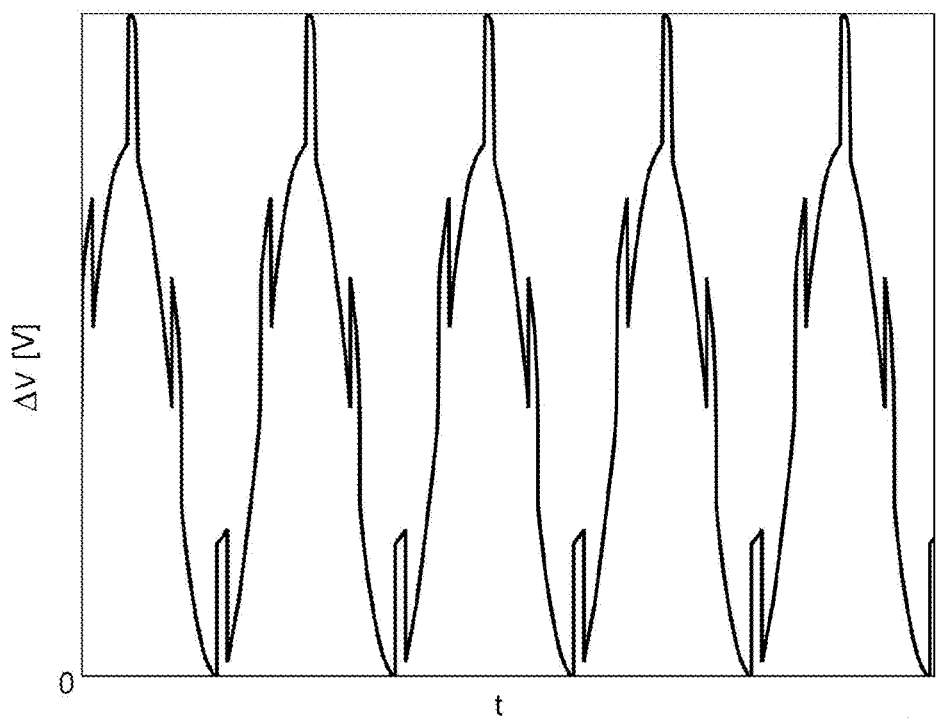
Figure 9C:
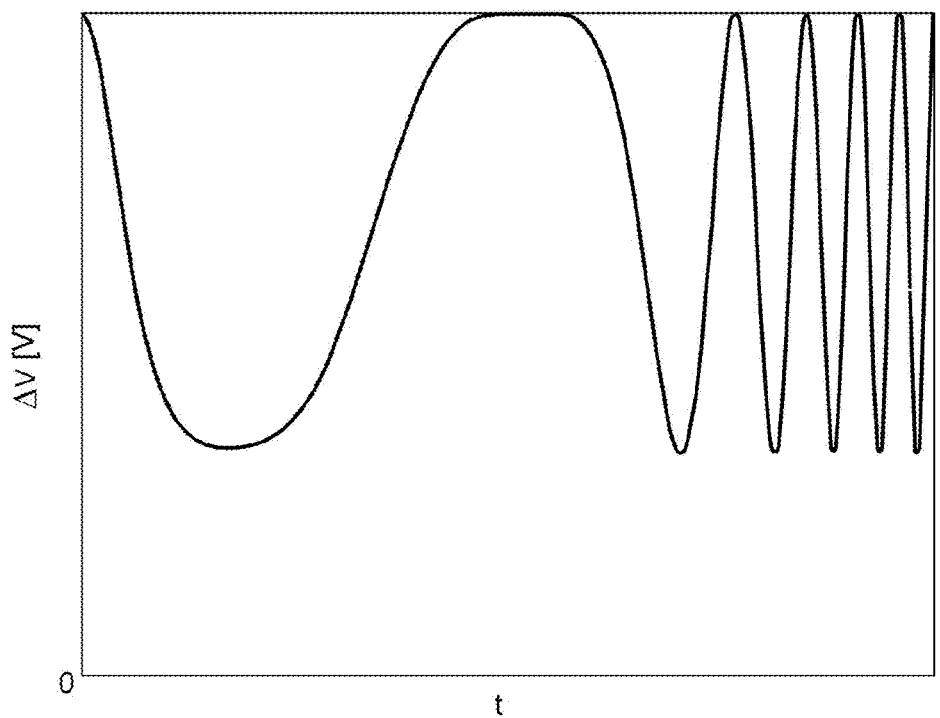

FIGS. 9a, 9b, 9c illustrate examples of waveforms for the potential difference ΔV(t) applied to the single control electrode 19, to obtain, respectively: an impulsive control (FIG. 9a) of the first channel, with drops, or packets, of the first fluid $F_1$ that are, with a periodicity determined by the duty cycle of the waveform, mixed with the second fluid $F_2$ (the second channel is in this case always open); a control in a sinusoidal regime (FIG. 9b) of the second channel, with the first channel once again controlled intermittently, thus obtaining a mixing with a controlled ratio of packets of the first and second fluids $F_1$, $F_2$; and a frequency control (FIG. 9c), with time-variable ratio of the mixed amounts of the first and second fluids $F_1$, $F_2$.

In general, the possibility of adjustment afforded through the control of the potential difference ΔV(t) is moreover suited to implementation of a closed-loop feedback control.

Figure 10:
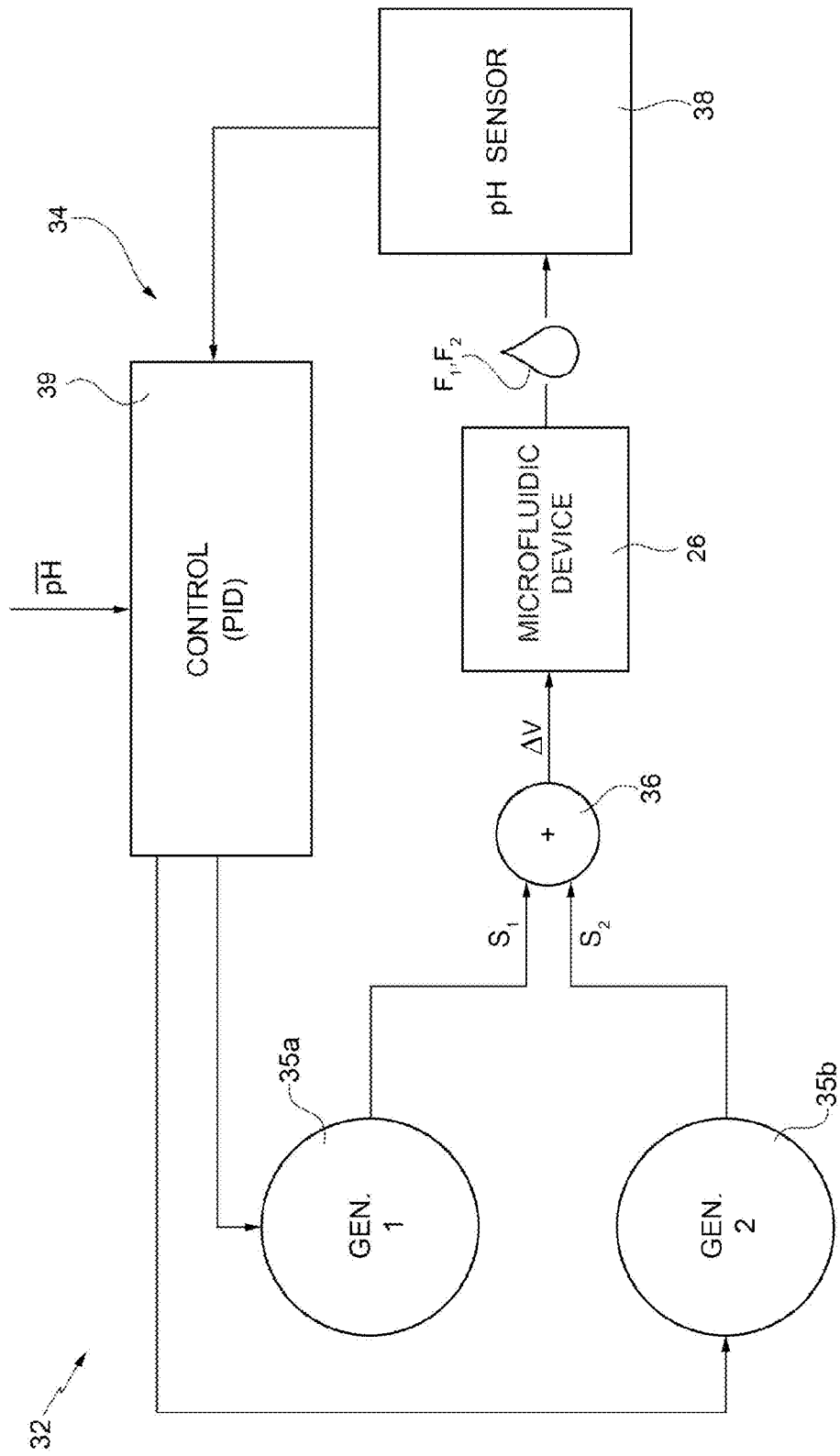
FIG. 10 shows a block diagram of a microfluidic analysis system, according to a further aspect of the invention.

FIG. 10 illustrates, in this regard, a simplified block diagram of a possible microfluidic system 32, having analysis functions, which includes the microfluidic device 26 illustrated previously and a closed-loop control circuit 34.

In detail, the control circuit 34 comprises: a first signal generator 35a, which is designed to generate a first control signal $S_1$ for control of the first mixing channel; a second signal generator 35b, which is designed to generate a second control signal $S_2$ for control of the second mixing channel; a combination unit 36 for combination of the first and second control signals $S_1$, $S_2$ and generation of the potential-difference signal ΔV(t), which is applied to the single control electrode 19 (here not illustrated) of the microfluidic circuit 10.

The control circuit 34 further comprises: a sensor element 38, for example, a pH sensor, in the case where the mixture of the first and second fluids $F_1$, $F_2$ is preferred to have a controlled pH, the sensor element 38 being designed to measure the pH of the mixture of fluids; and a control unit 39, for example of a PID (Proportional Integral Derivative) type, which receives the measurements detected by the sensor element 38 and is designed to control the first and second signal generators 35a, 35b as a function of the deviation of the measured pH from a target value pH, thus providing a closed-loop feedback control.

Figure 11:
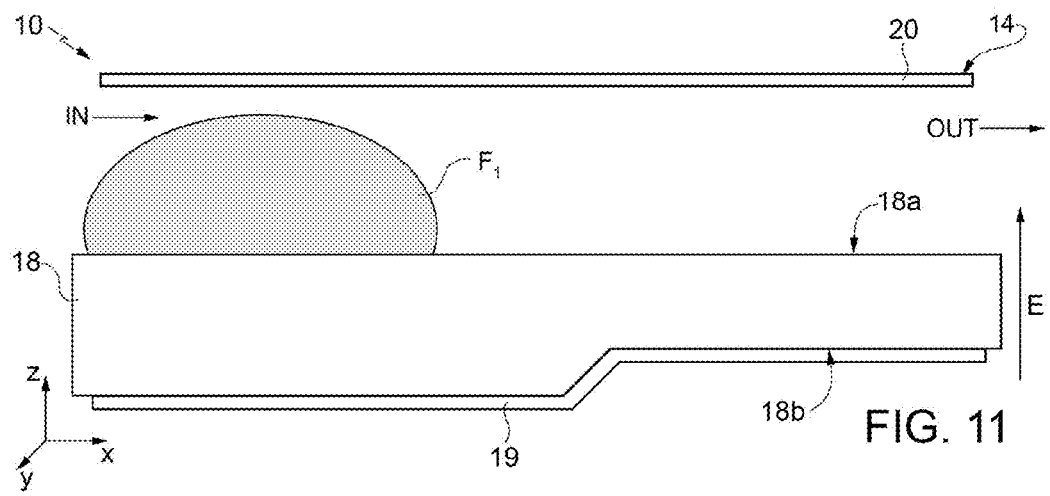
FIG. 11 is a cross section of a microfluidic circuit according to a further embodiment of the invention.

With reference to FIG. 11, a different embodiment of the microfluidic circuit is now discussed, designated once again by 10, where the spatially variable conformation of the dielectric layer 18 is determined by the spatially variable profile of the bottom surface 18b of the dielectric layer 18, whereas the top surface 18a is substantially planar in the horizontal plane xy.

Consequently, the first electrode 19 of the electrode structure 14 also has a corresponding spatially variable conformation.

Altogether similar considerations apply also in this case, as regards the variability of electrowettability as a function of the potential difference ΔV(t) applied to the electrode structure 14 and of the spatially variable profile of the dielectric layer 18.

In particular, it may be noted that in this case a channel region for "virtual" confinement of the fluid $F_1$ is defined on the substantially planar top surface 18a of the dielectric layer 18, with electrowettability variable according to the spatially variable conformation of the bottom surface 18b of the dielectric layer 18.

Figure 12:
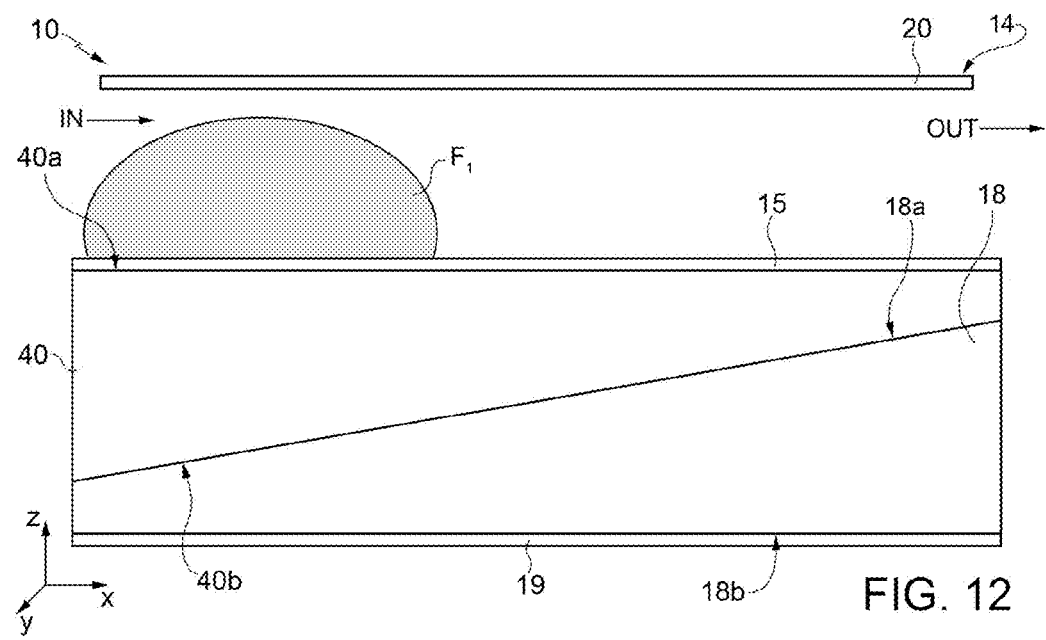
FIG. 12 is a cross section of a microfluidic circuit according to yet a further embodiment of the invention.

FIG. 12 shows a further embodiment of the microfluidic circuit, once again designated by 10.

In this variant, the dielectric structure 12 of the microfluidic circuit 10 moreover comprises a further dielectric layer 40 and a possible supporting layer 15, which is also made of dielectric material.

The dielectric layer 18 has a first relative permittivity $\in_{r1}$, and the further dielectric layer 40 has a second relative permittivity $\in_{r2}$ different from, for example less than, the first relative permittivity $\in_{r1}$.

The spatially variable conformation of the dielectric structure 12 is given in this case by the contact surface, or interface surface, between the dielectric layer 18 and the further dielectric layer 40, having a spatially variable profile.

This contact surface coincides, in the embodiment illustrated in FIG. 12, with the top surface 18a of the dielectric layer and moreover with a respective bottom surface 40b of the further dielectric layer 40. Both the bottom surface 18b of the dielectric layer 18 and a respective top surface 40a of the further dielectric layer 40 are substantially planar, parallel to the horizontal plane xy.

The bottom surface 18b of the dielectric layer 18 is in contact with the first control electrode 19, whereas the top surface 40a of the further dielectric layer 40 is in this case in contact with the supporting layer 15, which has electrowetting characteristics and defines the area for transport of the fluid.

It is to be noted that the supporting layer 15 may possibly not be present, when the further dielectric layer 40 includes electrowettable material.

In the embodiment illustrated in FIG. 12, the aforesaid contact surface between the dielectric layers 18 and 40 has a continuous planar profile in a plane inclined by a certain non-zero angle with respect to the horizontal plane xy, hence defining a line with constant slope in the cross section shown in FIG. 12.

It should hence be noted that the resulting capacitor defined between the first control electrode 19 and the reference electrode 20 may not be a plane capacitor, in so far as the contact surface between the dielectric layers is not parallel to the plane of the electrodes.

Figure 13:
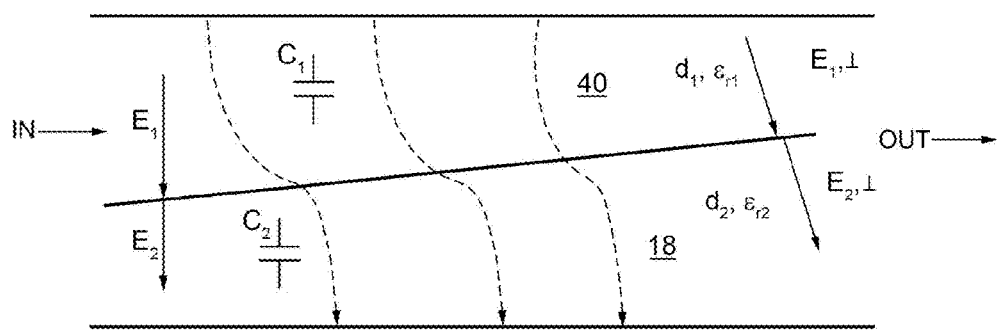
FIG. 13 shows schematically the pattern of field lines in the microfluidic circuit of FIG. 12.

Also with reference to FIG. 13, it may be noted that the dielectric layers 18, 40 have a respective first thickness $d_1(x)$ and second thickness $d_2(x)$, variable point by point continuously as a function of the position along the horizontal axis x.

Moreover, it may be noted that the lines of the electric field E bend at the contact surface in order to satisfy the interface condition:

$$\in_{r1} \cdot E_{1,\perp} = \in_{r2} \cdot E_{2,\perp}$$

where $E_{1,\perp}$ and $E_{2,\perp}$ are the components of electric field orthogonal to the contact surface, respectively, in the further dielectric layer 40 and in the dielectric layer 18 (the parallel components being, instead, the same as one another).

In the example illustrated, the condition moreover applies:

$$E_{1,\perp} < E_{2,\perp}$$

in so far as $\in_{r1} > \in_{r2}$.

Moreover, it may be noted that the capacitances per unit area of the dielectric layers 18, 40, designated respectively by $C_1$ and $C_2$, vary along the horizontal axis x.

In order to estimate the intensity of the electric field E, the approximation of planar capacitors may be used; for example, the electric field $E_1$ on the further dielectric layer 40, which determines the electrowetting properties with respect to the liquid, is given by the expression $$E_1(x, t) = \frac{\Delta V(t)}{d_1(x)} \frac{C_2(x)}{C_1(x) + C_2(x)}$$

being hence evidently variable in time, as a result of the variability of the potential difference $\Delta V(t)$, and in space, owing to the spatially variable conformation of the dielectric structure 12.

It should be noted that the aforesaid equation does not take into account the presence of the supporting layer 15, for convenience of illustration; however, altogether similar considerations apply also in the latter case.

Moreover, it is thus possible to control precisely the electrowetting characteristics on the surface, and hence the characteristics of movement of the fluid $F_1$ when present on the supporting layer 15 or on the top surface 40a of the further dielectric layer 40 (if the same dielectric layer is wettable), as a function of the potential difference $\Delta V(t)$ applied to the electrode structure 14, and as a function of the geometrical parameters of the spatially variable conformation of the dielectric structure 12.

In the embodiment illustrated in FIGS. 12 and 13, the electric field felt by the fluid $F_1$ for increasing values of the potential difference $\Delta V(t)$ applied to the electrode structure 14 is such that the electrowettability increases progressively, being in any case lower towards the outlet OUT of the microfluidic circuit 10. Consequently, as the voltage value increases, the fluid $F_1$ progressively occupies the virtual channel that has formed on the top surface, moving from the inlet IN to the outlet OUT.

The embodiment just illustrated has the advantage that also the surface for transport of the fluid is planar, favoring the growth of possible other structures on the same transport surface.

Figure 14:
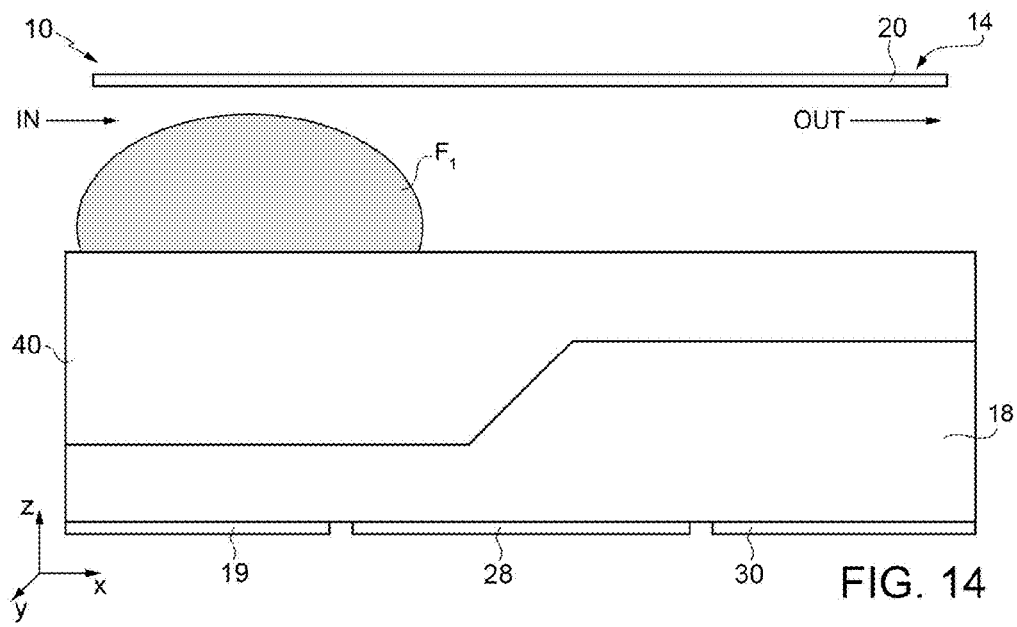
FIG. 14 is a cross section of a microfluidic circuit according to yet a further embodiment of the invention.

It is clear that further embodiments may likewise be envisaged, having different spatially variable profiles of the contact surface between the first and second dielectric layers 18, 40 (for example, a step-like profile, as illustrated in FIG. 14), and/or a greater number of control electrodes (as illustrated once again in FIG. 14) and/or a different number of stacked dielectric layers that are designed to constitute as a whole the dielectric structure 12.

Figure 15:
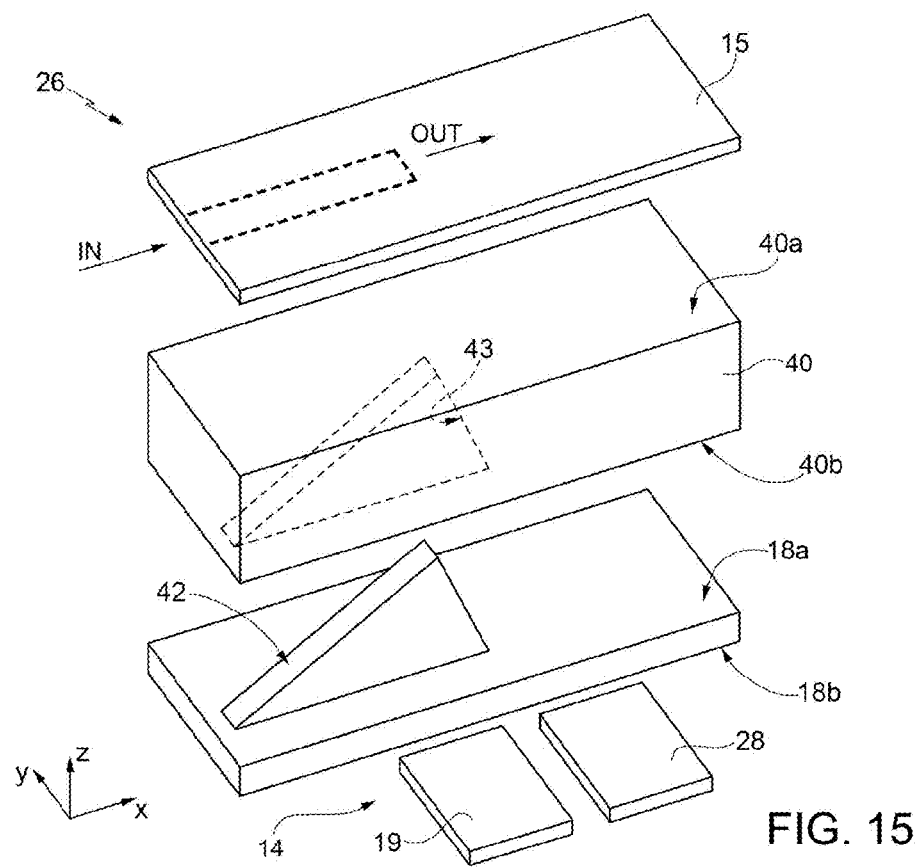
FIG. 15 is an exploded schematic view of a microfluidic circuit similar to the microfluidic circuit shown in FIG. 12.

FIG. 15 is a schematic perspective illustration of a microfluidic device, designated once again by 26, which includes the microfluidic circuit 10 of FIG. 12.

In particular, FIG. 15 shows, with a dashed line: the virtual channel that is formed on the surface of the supporting layer 15 (or, in the case where this is not present, on the top surface 40a of the further dielectric layer 40, having in this case electrowetting properties); the projecting ramp structure, here designated by 42, formed on the top surface 18a of the dielectric layer 18, and the corresponding cavity or recess 43 that is formed in the bottom surface 40b of the further dielectric layer 40 in order to define the spatially variable conformation of the dielectric structure 12; and the underlying electrode structure 14, in this case formed by a first control electrode 19 and by a second control electrode 28, which are designed to control respective functional areas, or fluid-transport regions, of the microfluidic device 26.

In particular, in a way similar to what has been illustrated previously, the first control electrode 19 may be controlled (for example, with a closed-loop feedback circuit) to obtain a controlled transport of fluid $F_1$ from the inlet IN to the outlet OUT of the microfluidic circuit 10, and the second control electrode 28 may be actuated for obtaining transfer of fluid $F_1$ from the outlet OUT of the microfluidic circuit 10 to a further functional region of the microfluidic device 26, for example to a further microfluidic circuit (not illustrated), an analysis chamber (not illustrated), or a reservoir (not illustrated, either).

Figure 16:
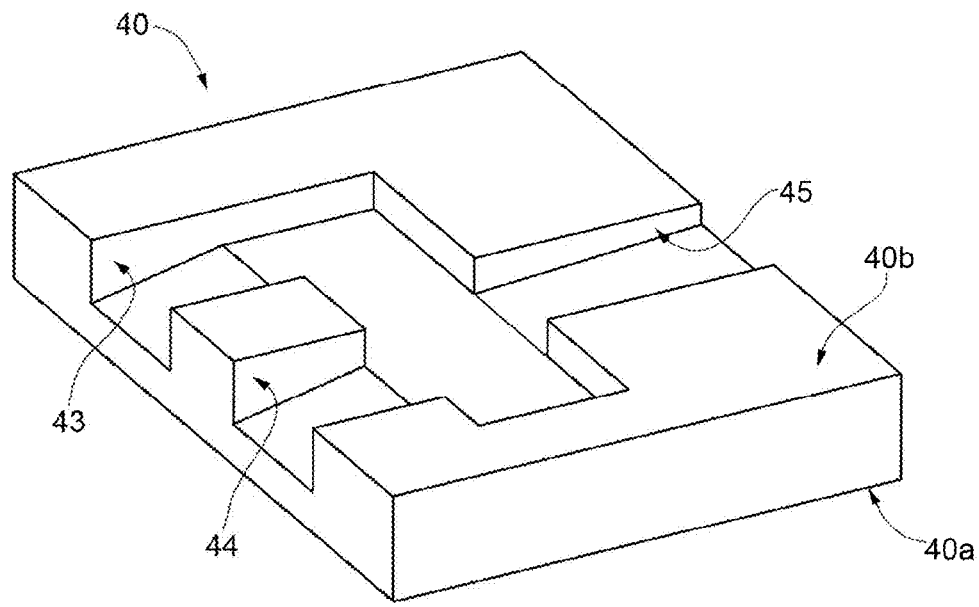
FIG. 16 is a perspective view of a dielectric layer of the microfluidic circuit, according to a further aspect of the invention.

FIG. 16 shows, in a simplified perspective view, a further possible embodiment, regarding just the further dielectric layer 40, defined in which are three distinct cavities: a first cavity, designated once again by 43, and a second cavity 44 and a third cavity 45, which have a different slope and inclination with respect to the horizontal plane xy, and are designed to define different spatially variable conformations of the dielectric structure 12 for corresponding functional regions of the microfluidic device 26.

Figure 17:
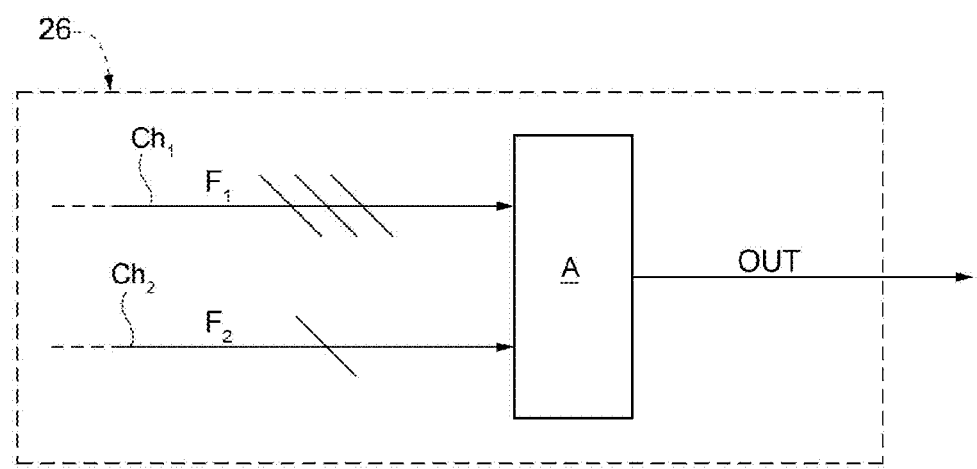
FIG. 17 is a schematic representation of a microfluidic circuit having a mixer function.

For example, the conformation illustrated may be used to obtain a mixer device (in a way alternative to what has been discussed previously with reference to FIGS. 7a-7c and 8), the block diagram of which is illustrated schematically in FIG. 17.

The first and second cavities 43, 44 may hence define, by means of the respective spatially variable conformations, a first channel and a second channel, respectively, for controlled transport of a first fluid and a second fluid, designated once again by $F_1$ and $F_2$, coming from a respective inlet of the microfluidic device 26, while the third cavity 45 may define a collection region for mixing of the two fluids $F_1$ and $F_2$ and transport of the resulting mixed fluid towards an outlet OUT of the microfluidic device 26.

Figure 18A:
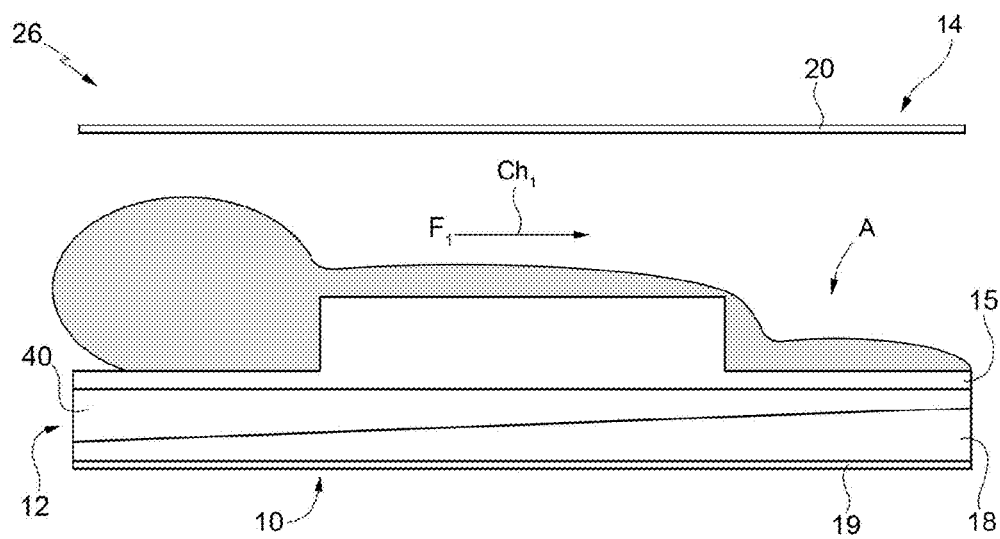
FIGS. 18a and 18b show different cross sections of the microfluidic circuit of FIG. 17.
Figure 18B:
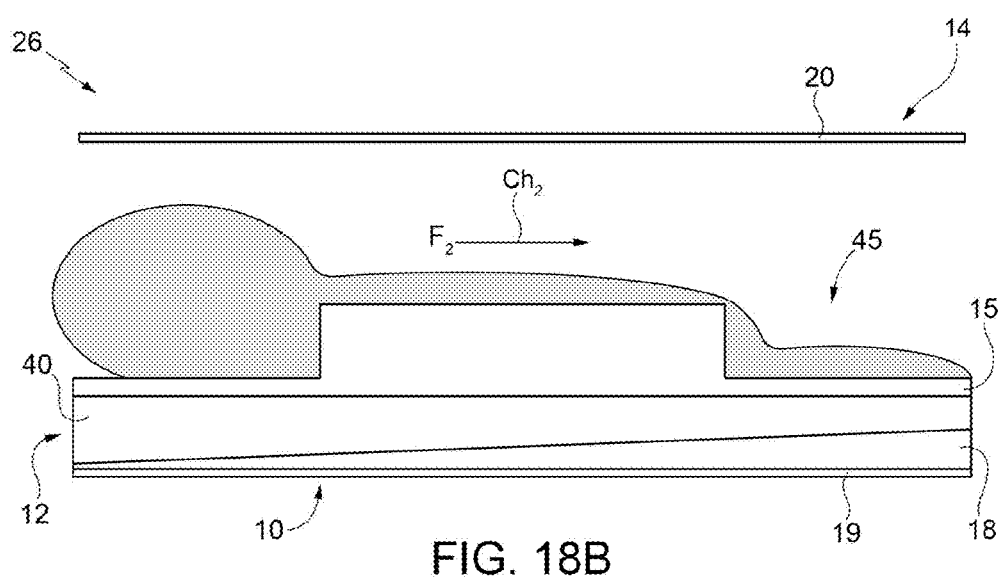

FIGS. 18a and 18b illustrate by way of example possible spatially variable conformations of the dielectric structure 12 of the first and second channels, respectively, here designated by $Ch_1$ and $Ch_2$, of the microfluidic device 26, which in this case differ as regards the different thickness of the respective dielectric layers 18, 40, the inclination of the contact surface, and/or the different values of the dielectric permittivity of the same dielectric layers 18, 40.

Given a same potential difference $\Delta V(t)$ applied to a same first control electrode 19 (which may be in common for the first and second channels $Ch_1$ and $Ch_2$), the electrowetting properties of the first and second channels hence differ as a function of the different spatial conformation of the corresponding dielectric structure 12, thus determining different transport modes (for example, in terms of a relative amount of transported fluid) for the fluids $F_1$, $F_2$, and a desired mixing ratio at the collection region, here designated by A.

A single control electrode 19 may be coupled to the bottom surface of the dielectric layer 18 (common to both of the channels).

As shown in FIGS. 18a, 18b, in this embodiment, the supporting layer 15 has at the center a raised portion. Once again, the dielectric structure is shaped for defining an energy barrier for movement of the fluids $F_1$, $F_2$ towards the collection area. In particular, application of an electric field of a sufficient and controlled value enables the fluids to get over the energy barrier and to mix in the collection area A.

Figure 19A:
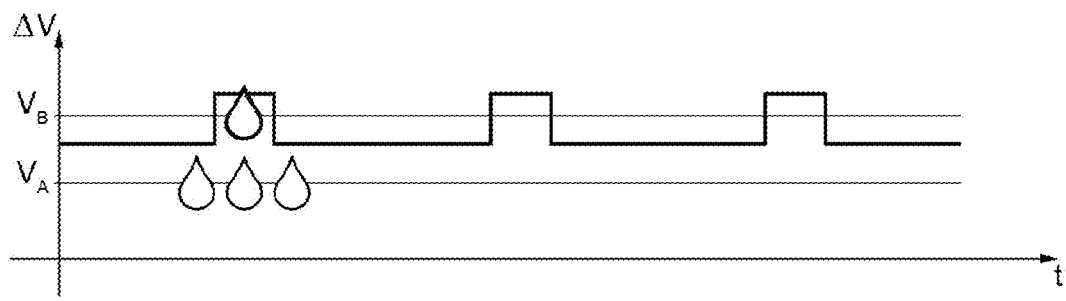
FIGS. 19a and 19b are plots of quantities related to the microfluidic circuit of FIG. 17.

FIG. 19a shows, by way of example, a possible time plot of the potential difference $\Delta V(t)$ applied to the single control electrode 19.

The voltage signal may have an impulsive plot, having a controllable duty cycle, and may have a first value, higher than a first threshold voltage $V_A$ and lower than a second threshold voltage $V_B$, and a second value, higher that the second threshold voltage $V_B$.

In particular, the first threshold voltage $V_A$ is sufficient to give rise to electrowettability of the supporting layer 15 at the first channel $Ch_1$ (which is always open), but not at the second channel $Ch_2$, which is electrowettable when the second threshold $V_B$ is exceeded (and is hence opened or closed intermittently).

Figure 19B:
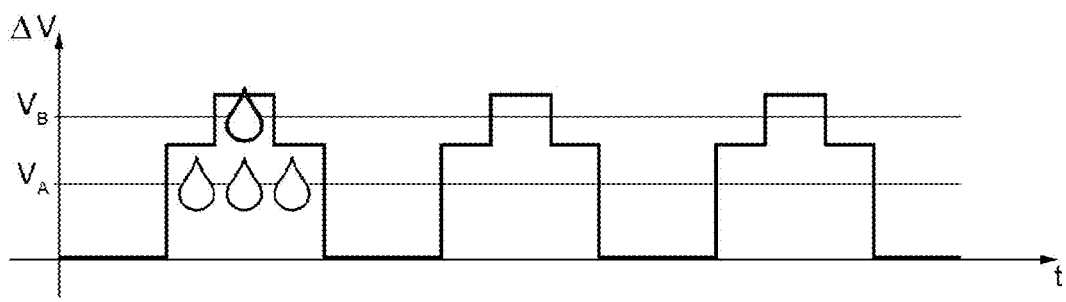

FIG. 19b illustrates a further possible plot of the potential difference $\Delta V(t)$ applied to the single control electrode 19, in this case with intermittent control of both of the channels $Ch_1$ and $Ch_2$.

It is hence evident how it is possible to control precisely mixing of the two fluids $F_1$, $F_2$, in variable and desired proportions by control of the amplitude and of the duty cycle of the potential-difference signal $\Delta V(t)$ applied to the single control electrode 19.

The process for manufacturing the dielectric structure 12 of the previously described microfluidic circuit 10 may generally envisage:

depositing the dielectric layer 40, and subsequently patterning the layer to obtain the first cavity 43 (and possibly further cavities, such as the second and third cavities 44, 45, having the desired shape, dimensions, and position);

depositing the dielectric layer 18 in such a way as to fill the first cavity 43 (and possibly the further cavities) and define in the resulting dielectric structure 12 a spatially variable dielectric profile; and in the case where it is present, depositing the supporting layer 15 on the top surface 40a of the further dielectric layer 40.

In a possible embodiment, the further dielectric layer 40 may be made of a first polymeric, or polymeric-ceramic material. The patterning step may be carried out according to one of the following techniques: soft lithography; etching with micrometric or nanometric tips that are heated and moved around; focused-ion-beam etching.

Among the possible materials are the thermoplastic materials known as "polyaryletherketones", characterized by a good resistance to temperature. Another example is the siloxane bisbenzocyclobutene, which possesses excellent characteristics of thermal and dielectric stability, or the poly-dimethyl-siloxane (PDMS).

As previously mentioned, in the case where the supporting layer 15 is not envisaged, the material of the further dielectric layer 40 has electrowetting characteristics.

The dielectric layer 18 may be made of a second polymeric, or polymeric-ceramic material, having a temperature of vitreous transition or cross-linking (also referred to as "hardening", or "vulcanization", or "curing") lower than the melting temperature of the first polymeric material. In addition, it is convenient for the second polymeric material to have a dielectric constant sufficiently different from the first.

The conditions of cross-linking for the second polymeric material, in terms of temperature and duration, take into account the fact that, generally, the first material, when it is polymeric, may already undergo, at temperatures lower than the melting point, an increase in viscosity (vitreous transition), which, albeit not representing a proper transition of state, may lead to modifications of the profiles previously etched. This being taken into account, for cross-linking of the second material, processes involving longer duration and lower temperatures are preferred. In the case where it is found experimentally that cross-linking of the second material will in any case modify, at least partially, the etched surface of the first material, it is possible to compensate this modifications beforehand, taking them into account in the provision of the first layer, for example, producing deeper etches and/or ones having a profile that is partially different from the desired final result (that will be obtained subsequently, after cross-linking of the second material).

An example of second polymeric material is the benzocyclobutene, where nanoparticles of barium titanate have been dispersed.

The second polymeric material may hence be deposited in the liquid state on top and in contact with the etched surface of the dielectric layer 40, for example using sputtering techniques. Subsequently, it is possible to carry out a cross-linking at the respective cross-linking temperature to obtain the dielectric layer 18.

The advantages of the described solution emerge clearly from the foregoing discussion.

In particular, the movement of the fluid in the fluidic circuit is controlled with greater resolution and accuracy thanks to the control and regulation of the voltage applied to the electrodes, as a function of the spatially variable profile of the dielectric structure.

The spatial resolution with which this profile is obtained is high, as is likewise the precision with which the control of voltage, amplitude, frequency, and/or other parameters of the waveform of the potential difference applied is carried out.

Moreover, it is convenient to implement a closed-loop feedback control, based on one or more detectable parameters of the fluid in order to further increase the precision of the microfluidic system.

The possibility of controlling the microfluidic circuit using a single electrode enables a considerable reduction in the complexity of the wiring.

In general, the dimensions and complexity of implementation of the microfluidic circuit are considerably reduced as compared to traditional solutions, and enable convenient on-chip integration thereof (possibly, together with control circuits and/or further devices and sensors).

In this regard, FIG. 20 shows schematically the microfluidic device 26 integrated in a die 50 including semiconductor material.

The first control electrode 19 (and, where present, further control electrodes) is (are) coupled to a substrate 52 of the die 50, and electrical-connection paths 54 enable biasing of the electrode structure by a biasing circuit (not illustrated) of the microfluidic device 26, possibly integrated in the same die 50, or in a different die (not illustrated).

The reference electrode 20 may be integrated in a different die, or else in the same die 50, appropriately suspended over the substrate 52, by means of a mechanical suspension structure (not illustrated).

Finally, it is clear that modifications and variations may be made to what has been described and illustrated herein, without thereby departing from the scope of the present invention, as defined in the annexed claims.

In particular, it is underlined once again that the actual embodiment of the spatially variable dielectric profile of the dielectric structure 12 of the microfluidic circuit 10 may vary with respect to the embodiments illustrated, according to the specific design requirements, for example as regards the materials used, the number of dielectric layers, and the geometrical conformation of the individual dielectric layers.

In general, the spatially variable dielectric profile of the dielectric structure 12 may be determined by any combination of one or more of the following factors, or other factors that are not listed here but that will be evident to a person skilled in the field: a spatially variable conformation of the dielectric structure 12 (for example, defined by a spatially variable profile of one or more surfaces of the single and/or of the further dielectric layer 18, 40); and a spatial gradient of the dielectric permittivity of the dielectric structure 12.

Moreover, also the number and arrangement of the control electrodes may vary with respect to what has been illustrated.

What has been described previously may moreover apply to integrated fluidic circuits having a smaller dimensional scale, for example a nanometric scale.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An integrated fluidic circuit, comprising:
a dielectric structure having a supporting surface designed to support, at a first functional region, a first fluid that is to be moved along a first fluid path, and at a second functional region, a second fluid that is to be moved along a second fluid path, the first and second fluid paths being transverse to one another;
an electrode structure operatively coupled to the dielectric structure and configured to generate at the first functional region an electric field designed to modify electrowetting properties of an interface between the first fluid and the supporting surface, the electrode structure including a first electrode spaced apart from the dielectric structure,
wherein the dielectric structure includes:
a first dielectric layer at the first functional region, the first dielectric layer having a first thickness and a second thickness that is different from the first thickness, the first dielectric thicknesses corresponding to a spatially variable profile of said electric field that affects said electrowetting properties of the interface between the first fluid and the supporting surface; and
a second dielectric layer at the second functional region, the second dielectric layer having a uniform thickness along the second fluid path.

2. The circuit according to claim 1 wherein said electrode structure includes the first electrode having a main extension in a horizontal plane; and the first dielectric layer having an inclined ramp in the first functional region, inclined with respect to said horizontal plane.

3. The circuit according to claim 2 wherein said electrode structure includes a second electrode with an extension in a second plane parallel to the horizontal plane; and a first surface of the first dielectric layer is closer to the first electrode than a second surface of the first dielectric layer, the second surface having a planar extension in said horizontal plane, that is opposite to the first surface, the second surface in contact with the second electrode.

4. The circuit according to claim 2 wherein said dielectric structure includes a third dielectric layer having a respective first surface, the third dielectric layer having a first thickness and a second thickness that is different from the first thickness, the first surface being in contact with a first surface of the first dielectric layer, the third dielectric layer having an inclined ramp in the first functional region, inclined with respect to said horizontal plane.

5. The circuit according to claim 4 wherein the third dielectric layer has a respective second surface, having a planar extension in said horizontal plane, that is opposite to the respective first surface, and wherein the first dielectric layer has the second surface, having a planar extension in said horizontal plane, that is opposite to a first main surface in contact with the first electrode.

6. The circuit according to claim 5 wherein said first dielectric layer and said third dielectric layer have a first dielectric permittivity in a first direction orthogonal to said horizontal plane that is variable along a second direction in said horizontal plane.

7. The circuit according to claim 1 wherein a voltage across the electrode structure includes a first voltage at a first time and a second voltage at a second time.

8. The circuit according to claim 1 wherein the electrode structure includes a single control electrode configured to receive a potential-difference signal to generate a respective spatially variable profile of the electric field at the first and second functional regions.

9. The circuit according to claim 8 wherein the generated electric field being configured to mix the first fluid and the second fluid.

10. The circuit according to claim 9 wherein the first and second fluids are mixed in a third functional region, the dielectric structure configured to channel the first fluid from the first functional region to the third functional region and the second fluid from the second functional region to the third functional region.

11. A microfluidic system, comprising
an integrated fluidic circuit including:
a dielectric structure having a supporting surface of an electrowettable material on a first side of the dielectric structure, the dielectric structure having a first portion having a first uniform thickness, a second portion having a second uniform thickness, the second thickness being different than the first thickness, and a third portion between the first portion and the second portion, the third portion having a varying thickness that varies from the first uniform thickness to the second uniform thickness;
a first electrode structure separated from the dielectric structure by a gap;
a second electrode structure on a second side of the dielectric structure, the second electrode structure overlaps the first portion, the third portion, and a first part of the second portion; and
a third electrode structure on the second side of the dielectric structure, the second electrode and third electrode being spaced from each other, the third electrode structure overlaps a second part of the second portion, the supporting surface being between the first electrode structure and the second and third electrode structures; and
an electronic control circuit coupled to the integrated microfluidic circuit to control movement of said first fluid, said electronic control circuit being configured to supply a potential-difference signal to the first electrode structure and the second electrode structure to generate the electric field.

12. The system according to claim 11 wherein said electronic control circuit is configured to control a value of said potential-difference signal based on the varying thickness between the second electrode and the supporting surface.

13. The system according to claim 12 wherein said electronic control circuit is configured to control one or more of the amplitude, frequency, and duty cycle of a waveform of said potential-difference signal.

14. The system according to claim 12 wherein said electronic control circuit is configured to implement a closed-loop control of the value of said potential-difference signal based at least in part on a measured characteristic of said first fluid.

15. The system according to claim 11 wherein said integrated microfluidic circuit is a controlled-flow valve or a mixer of controlled flows.

16. A method, comprising:
injecting a first fluid into an inlet of a first fluid path of an integrated fluidic circuit;
injecting a second fluid inlet of a second fluid path of the integrated fluidic circuit, the second fluid path being transverse to the first fluid path;
generating an electric field at a first functional region and a second functional region of a dielectric structure in the integrated fluid circuit, the first functional region having a first thickness and a second thickness that is different than the first thickness, the first functional region corresponding to at least a portion of the first fluid path and the second functional region corresponding to at least a portion of the second fluid path, the generating including:
supplying a voltage across a first electrode that is separated from the dielectric structure by a gap, the first electrode overlapping and interacting with the first and the second functional regions, and across a second electrode that corresponds to the first functional region, and across a third electrode that corresponds to the second functional region, the second electrode separated from the first electrode by the first functional region of the dielectric structure, the electric field modifying the electrowetting properties between the first fluid and a supporting surface in the first functional region and the second fluid and a supporting surface in the second functional region; and
controlling a value of the voltage across said first and second electrodes in the first functional region based at least in part on the first and second thicknesses.

17. The method according to claim 16 wherein the controlling the value of the voltage across said first and second electrodes includes controlling one or more of an amplitude, frequency, and duty cycle of the voltage.

18. A microfluidic device, comprising:
a first dielectric layer having a first region and a second region, the first region having a first thickness and the second region having a second thickness, the second thickness being greater than the first thickness, the first dielectric layer including a ramp that connects the first region of the first dielectric layer to the second region of the first dielectric layer;
a second dielectric layer on the first dielectric layer, the second dielectric layer having a planar top surface that extends over the first region, the ramp, and the second region;
a first electrode in direct contact with the first dielectric layer; and
a second electrode facing the second dielectric layer and separated from the top surface by a gap, the second electrode being capacitively coupled to the first electrode.

19. The microfluidic device of claim 18, further comprising:
a third electrode under a third region of the first dielectric layer, the third electrode on a same side of the first dielectric layer as the first electrode, and the second electrode capacitively coupled to the third electrode.

20. The system of claim 11 wherein the second electrode structure is configured to be coupled to the first electrode structure to generate an electric field at a first functional region to modify electrowetting properties of a first fluid between the first electrode structure and the supporting surface, the third portion of the dielectric structure being between the second electrode and the supporting surface in the first functional region, the varying thickness being configured to affect the electric field between the first and second electrode structures.

* * * * *

UNITED STATES PATENT AND TRADEMARK OFFICE
CERTIFICATE OF CORRECTION

| | |
|---|---|
| PATENT NO. | : 9,983,169 B2 |
| APPLICATION NO. | : 14/489310 |
| DATED | : May 29, 2018 |
| INVENTOR(S) | : Alessandro Paolo Bramanti |

It is certified that error appears in the above-identified patent and that said Letters Patent is hereby corrected as shown below:

Column 15, Line 64:
"injecting a second fluid inlet of a second fluid path of the" should read, --injecting a second fluid into an inlet of a second fluid path of the--.

Signed and Sealed this
Thirtieth Day of April, 2019

Andrei Iancu
*Director of the United States Patent and Trademark Office*